United States Patent [19]
Mittelstadt et al.

[11] Patent Number: 6,033,415
[45] Date of Patent: Mar. 7, 2000

[54] SYSTEM AND METHOD FOR PERFORMING IMAGE DIRECTED ROBOTIC ORTHOPAEDIC PROCEDURES WITHOUT A FIDUCIAL REFERENCE SYSTEM

[75] Inventors: Brent D. Mittelstadt, Placerville; Steven M. Cohan, Woodland, both of Calif.; Steve Schreiner, Wilbraham, Mass.

[73] Assignee: Integrated Surgical Systems, Davis, Calif.

[21] Appl. No.: 09/152,359

[22] Filed: Sep. 14, 1998

[51] Int. Cl.$^7$ ........................................ A61B 19/00
[52] U.S. Cl. ........................ 606/130; 128/922; 600/425
[58] Field of Search ..................... 606/1, 130; 128/920, 128/922; 600/425, 429

[56] References Cited

U.S. PATENT DOCUMENTS

| | | | |
|---|---|---|---|
| 4,146,924 | 3/1979 | Birk et al. ................................. | 364/513 |
| 4,373,532 | 2/1983 | Hill et al. ................................. | 128/660 |
| 4,841,975 | 6/1989 | Woolson ................................. | 128/653 |
| 4,932,414 | 6/1990 | Coleman et al. ....................... | 128/660 |
| 4,945,914 | 8/1990 | Allen ....................................... | 128/653 |
| 4,991,579 | 2/1991 | Allen ....................................... | 128/653 |
| 5,016,639 | 5/1991 | Allen ....................................... | 128/653 |
| 5,086,401 | 2/1992 | Glassman et al. ....................... | 395/94 |
| 5,094,241 | 3/1992 | Allen ....................................... | 128/653 |
| 5,097,839 | 3/1992 | Allen ....................................... | 128/653.1 |
| 5,119,817 | 6/1992 | Allen ....................................... | 128/653.1 |
| 5,142,930 | 9/1992 | Allen et al. ............................. | 74/469 |
| 5,161,536 | 11/1992 | Vilkomerson et al. ................. | 128/660 |
| 5,167,165 | 12/1992 | Brucher et al. .......................... | 74/479 |
| 5,178,164 | 1/1993 | Allen ....................................... | 128/898 |
| 5,198,877 | 3/1993 | Schulz ..................................... | 356/375 |
| 5,211,164 | 5/1993 | Allen ....................................... | 128/653.1 |
| 5,222,499 | 6/1993 | Allen et al. ............................. | 128/653.1 |
| 5,230,338 | 7/1993 | Allen et al. ............................. | 1238/653 |
| 5,236,432 | 8/1993 | Matsen et al. ........................... | 606/88 |
| 5,249,581 | 10/1993 | Horbal et al. ........................... | 128/664 |
| 5,299,288 | 3/1994 | Glassman et al. ....................... | 395/80 |
| 5,306,306 | 4/1994 | Bisek et al. ............................. | 623/16 |

(List continued on next page.)

FOREIGN PATENT DOCUMENTS

| | | | |
|---|---|---|---|
| 647 428 A2 | 4/1995 | European Pat. Off. .................... | 6/12 |
| WO 91/07726 | 5/1991 | WIPO ....................................... | 15/72 |
| WO 94/17733 | 8/1994 | WIPO ....................................... | 6/12 |
| WO 97/09929 | 3/1997 | WIPO ....................................... | 5/103 |

OTHER PUBLICATIONS

Ault, et al., "Frameless patient registration using ultrasonic imaging", The Robotics Institute, School of Computer Science, Pittsburgh, Pennsylvania, pp. 74–81.

Cain, et al., "Safety considerations in a surgical robot", Integrated Surgical Systems, Inc., Sacramento, California, Paper #93–035, pp. 291–294, (1993).

Champleboux et al., "An optical conformer for radiotherapy treatment planning", TIMC–IMAG, Facullté de Médecine de Grenoble, La Tronche, France, pp. 69–73.

Grimson, et al., "Automated registration for enchanced reality visualization in surgery", Visualization in Surgery, pp. 82–89.

(List continued on next page.)

Primary Examiner—Michael Buiz
Assistant Examiner—Julian W. Woo
Attorney, Agent, or Firm—Townsend Townsend & Crew LLP

[57] ABSTRACT

A method for transforming a bone image data set representing at least a partial image of a long bone to a robotic coordinate system, comprising: generating the bone image data set from a bone image; registering a bone digitizer arm to the robotic coordinate system; generating a digitized bone data set by taking bone surface position measurements with the digitizer arm; and transforming the bone image data set into the robotic coordinate system by performing a best-fit calculation between coordinates of the bone image data set and corresponding coordinates of the digitized bone data set.

26 Claims, 7 Drawing Sheets

U.S. PATENT DOCUMENTS

| | | | |
|---|---|---|---|
| 5,320,115 | 6/1994 | Kenna | 128/898 |
| 5,343,877 | 9/1994 | Park | 128/898 |
| 5,383,454 | 1/1995 | Bucholz | 128/653.1 |
| 5,394,875 | 3/1995 | Lewis et al. | 128/660.09 |
| 5,397,329 | 3/1995 | Allen | 606/73 |
| 5,408,409 | 4/1995 | Glassman et al. | 364/413.13 |
| 5,411,503 | 5/1995 | Hollstien et al. | 606/86 |
| 5,480,400 | 1/1996 | Berger | 606/60 |
| 5,524,180 | 6/1996 | Wang et al. | 600/118 |
| 5,546,942 | 8/1996 | Zhang | 128/653.1 |
| 5,564,437 | 10/1996 | Bainville et al. | 128/774 |
| 5,590,215 | 12/1996 | Allen | 382/128 |
| 5,649,021 | 7/1997 | Matey et al. | 382/128 |
| 5,682,886 | 11/1997 | Delp et al. | 128/653.1 |
| 5,696,837 | 12/1997 | Green | 382/128 |
| 5,806,518 | 9/1998 | Mittelstadt | 128/653.1 |

OTHER PUBLICATIONS

Kazanzides, et al., "Surgical and industrial robots: Comparison and case study", Integrated Surgical Systems, Inc., Sacramento, California, vol. 10, pp. 10–19 to 10–26 (circa 1994).

Kazanzides, et al., "Architecture of a surgical robot", IEEE Conference on Systems, Man, and Cybernetics, pp. 1624–1629, (1992).

Kazanzides, et al., "Force sensing and control of surgical robot", IEEE Intl. Conference on Robotics and Automation, pp. 612–617, (May 1992).

Lea, et al., "Registration and immobilization for robot-assisted orthopaedic surgery", Department of Mechanical Engineering, Northwestern University, Evanston, Illinois, pp. 63–68.

Lavallee, et al., "Computer assisted spine surgery: A technique for accurate transpedicular screw fixation using CT data and a 3–D optical localizer", TIMC, Faculte de Medecine de Grenoble, La Tronche, France, pp. 315–322 (1995).

Lombardi, Adolph V., "Cement removal in revision total hip arthroplasty", Seminars in Arthroplasty, 3(4):264–272, (Oct. 1992).

Mittelstadt et al., "Robotic surgery: Achieving predictable results in an unpredictable environment", Integrated Sujrgical Systems, Inc., Sacramento, California, pp. 367–372, (1993).

Mittelstadt et al., "The evolution of a surgical robot from prototype to human clionical use", Integrated Surgical Systems, Inc., Sacramento, California, pp. 36–41, (1994).

Mittelstadt et al., "Development of a surgical robot for cementless total hip replacement", Robotics, 11:553–560, (1993).

Nolte, et al., "A novel approach to computer assisted spine surgery", M.E. Muller Institute for Biomechanics, University of Bern, Bern, Switzerland a pp. 323–328 (1995).

Paul et al., "Development of a surgical robot for cemenntless totsl hip arthroplasty", Clinical Orthopaedics, 285:57–66, (1992).

Potamianos et al., "Intra–operative imaging guidance for keyhole surgery methodology and calibration", Robotics Group, Imperial College of Science, Technology and Medicine, London, United Kingdom, pp. 98–104.

Péria et al., "Accurate registration of SPECT and MR brian images of patients suffering from epilepsy or tumor", TIMB--TIMC–IMAG, Faculte de Medecine de Grenoble, LA Tronche, France pp. 58–62.

Simon, et al., "Techniques for fast and accurate intra–surgiocal registration", Robotics Institute, Carnegie Mellon University, Pittsburg, Pennsylvania, pp. 90–97.

SYSTEM AND METHOD FOR PERFORMING IMAGE DIRECTED ROBOTIC ORTHOPAEDIC PROCEDURES WITHOUT A FIDUCIAL REFERENCE SYSTEM

BACKGROUND OF THE INVENTION

1. Field of the Invention

The present invention relates generally to surgical methods and systems. More particularly, the present invention relates to a method and system for registering the position of a robotically manipulated surgical tool with a preoperative image by transforming a data set representing at least a partial image of a long bone to a robotic coordinate system.

Robotic systems for assisting in a number of medical procedures have been proposed, including neurosurgical, laparoscopic, and orthopedic procedures. While the details of a particular procedure may vary widely, a number of such procedures rely on first obtaining a preoperative image of the region to be operated on, and subsequently robotically controlling a medical tool based on information in the preoperative image. The procedures are usually surgical but can also be diagnostic. A need thus exists for transforming the preoperative image (usually in the form of a digital data set obtained by conventional imaging techniques) to a coordinate system employed by the robot. In this way, the robot is able to navigate the surgical tool based on the image data set which is representative of the patient's actual anatomy.

Of particular interest to the present invention, robotically assisted total hip replacement surgery is performed by first imaging the femur, typically by computerized tomography (CT), and producing a digital bone image data set representative of the femur. Selection and positioning of an implant within the femur is then planned at a computer workstation, such as the ORTHODOC™ presurgical planning workstation developed by Integrated Surgical Systems, Inc., Sacramento, Calif., assignee of the present application. Once the doctor has planned the implant placement on the workstation, a digital data set including both the image data (patient anatomy) and the planned positioning of the implant is produced. It is then necessary to transfer this data set to a computer-controlled robotic system intended to perform the surgery, such as the ROBODOC™ surgical robot system which has also been developed by Integrated Surgical Systems.

Successful hip replacement surgery, particularly when using cementless implants, relies on the highly accurate creation of a cavity within the proximal (upper) end of the femur for receiving the implant. Deviations less than ±1 mm from the planned cavity placement are desirable. A critical requirement in achieving such accuracy is precise registration between the bone image data set and the coordinate system of the surgical robot.

Image registration within the robotic coordinate system requires correlation between the physical position of the patient body site to be operated on, e.g., the femur in total hip replacement and knee replacement procedures, the digital bone image set representing the body feature, and the robotic coordinate system. Such correlation may be achieved by registering the bone image data set with the actual position of the body feature within the robotic coordinate space by physically contacting a probe at the end of a manipulator arm of the robot against certain imaged features on the body part. The information thus obtained by the robot controller can then be used to register the image with the actual body site, e.g., an immobilized femur, within the operative space of the robot.

Prior to the present invention, the ROBODOC™ surgical robot system has relied on the surgical implantation of a pair of metallic pins on the distal (lower) end of the femur and one additional metallic pin in the proximal end of the bone. These pins, usually referred to as fiducial markers, are readily apparent in the CT image of the bone and can thus be relied on to register the bone image with the robotic coordinate space by engaging a probe placed on the manipulator arm against each of the pins. Such registration is described in detail in Taylor et al. (1994) IEEE Trans. Robotics Automat. 10:261–275.

While capable of achieving a high degree of accuracy and precision, the need to implant the marker pins subjects the patient to considerable operative trauma. For that reason, it would be desirable to eliminate the implantation of fiducial marking pins altogether, yet provide a system for registering a bone image data set to a robotic coordinate system. The elimination of fiducial marking pins would offer numerous advantages including reducing the cost of the overall procedure, reducing the overall complexity of the treatment, and thereby reducing the risk to the patient. By eliminating one current surgical procedure, postoperative pain and discomfort would be substantially reduced.

A further advantage of eliminating fiducial marking pins is improved distal fixation, as follows. Currently, the distal femur is typically stabilized by securing the lower leg below the knee joint. Fixation of the lower leg below the knee joint is necessary when using fiduciary markers because the surgeon needs access to the marker pins during surgery. This method of knee fixation is non-optimal because the femur bone is on the opposite side of the knee joint which is relatively mobile such that the femur is not well stabilized. By eliminating fiducial marking pins, the distal femur could be fixated by securing the knee directly.

A further advantage of eliminating fiducial marking pins is that a computer tomography image of the bone can be taken at any convenient time prior to surgery, even several months prior to surgery. In contrast, when fiducial marking pins are used, it is necessary to take the computer tomography image shortly after the pins have already been attached. Accordingly, prior to the present invention, it has typically been necessary to undergo pin implantation, computerized tomography imaging of the bone, and robotic surgery all together within a relatively short time frame.

As will be explained, the present invention provides a system for registering a bone image to a robotic coordinate system in which the use of pre-inserted fiducial marking pins is eliminated, thereby overcoming numerous deficiencies in the prior art.

2. Description of the Background Art

The ORTHODOC™ presurgical planning workstation and the ROBODOC™ robotic surgical system are described in a number of references, including the following: (1) Kazanzides, P., Zuhars, J., Mittelstadt, B. D., Taylor, R. H.: "Force Sensing and Control for a Surgical Robot," *Proc. IEEE Conference. on Robotics & Automation,* Pages 612–616, Nice, France, May 1992. (2) Kazanzides, P., Zuhars, J., Mittelstadt, B. D., Williamson, B., Cain, P., Smith, F., Rose, L., Mustis, B.: "Architecture of a Surgical Robot," *Proc. IEEE Conference. on Systems, Man, and Cybernetics,* Chicago, Ill., Pages 1624–1629, October, 1992. (3) Paul, H. A., Bargar, W. L., Mittelstadt, B., Musits, B., Taylor, R. H., Kazanzides, P., Zuhars, J., Williamson, B., Hanson, W.: "Development of a Surgical Robot For Cementless Total Hip Arthroplasty," *Clinical Orthopaedics,* Volume 285, Pages 57–66, December 1992. (4) Kazanzides, P., Mittelstadt, B. D., Zuhars, J., Cain, P., Paul, H. A., "Surgical and Industrial Robots: Comparison and Case Study," *Proc. International Robots and Vision Automation Conference,* Pages 1019–1026, Detroit, Mich., April 1993. (5) Mittelstadt, B., Kazanzides, P., Zuhars, J., Williamson, B., Pettit, R., Cain, P., Kloth, D., Rose, L., Musits, B.: "Development of a surgical robot for cementless total hip replacement," *Robotica,* Volume 11, Pages 553–560, 1993. (6) Mittelstadt B., Kazanzides, P., Zuhars, J., Cain, P., Williamson, B.: "Robotic surgery: Achieving predictable results in an unpredictable environment," *Proc. Sixth International Conference on Advanced Robotics,* Pages 367–372, Tokyo, November, 1993. (7) Cain, P., Kazanzides, P., Zuhars, J., Mittelstadt, B., Paul, H.: "Safety Considerations in a Surgical Robot," *Biomedical Sciences Instrumentation,* Volume 29, Pages 291–294, San Antonio, Tex., April 1993. (8) Mittelstadt, B. D., Kazanzides, P., Zuhars, J., Williamson, B., Cain, P., Smith, F. Bargar, W.: "The Evolution of A Surgical Robot From Prototype to Human Clinical Use," in *Proc. First International Symposium on Medical Robotics and Computer Assisted Surgery,* Volume I, Pages 36–41, Pittsburgh, Pa., September 1994.

Other publications which describe image registration in robotic surgical and other procedures include the following: (9) Grimson, W. E. L., Lozano-Perez, T., Wells III, W. M., Ettinger, G. J., White, S. J., Kikinis, R.: "Automated Registration for Enhanced Reality Visualization in Surgery," *Proceedings of the First International Symposium on Medical Robotics and Computer Assisted Surgery,* Volume I, Sessions I–III, Pages 82–89, Pittsburgh, Pa., Sep. 22–24, 1995. (10) Nolte, L. P., Zamorano, L. J., Jiang, Z., Wang, Q., Langlotz, F., Arm, E., Visarius, H.: "A Novel Approach to Computer Assisted Spine Surgery," *Proceedings of the First International Symposium on Medical Robotics and Computer Assisted Surgery,* Volume II, Session IV, Pages 323–328, Pittsburgh, Pa., Sep. 22–24, 1994. (11) Lavallée, S., Sautot, P., Troccaz, J., Cinquin, P., Merloz, P.: "Computer Assisted Spine Surgery: a technique for accurate transpedicular screw fixation using CT data and a 3-D optical localizer," *Proceedings of the First International Symposium on Medical Robotics and Computer Assisted Surgery,* Volume II, Session IV, Pages 315–321, Pittsburgh, Pa., Sep. 22–24, 1994. (12) Potamianos, P., Davies, B. L., Hibberd, R. D.: "Intra-Operative Imaging Guidance For Keyhole Surgery Methodology and Calibration," *Proceedings of the First International Symposium on Medical Robotics and Computer Assisted Surgery,* Volume I, Sessions I–III, Pages 98–104, Pittsburgh, Pa., Sep. 22–24, 1994. (13) Simon, D. A., Hebert, M., Kanade, T.: "Techniques for Fast and Accurate Intra-Surgical Registration," *Proceedings of the First International Symposium on Medical Robotics and Computer Assisted Surgery,* Volume I, Sessions I–III, Pages 90–97, Pittsburgh, Pa., Sep. 22–24, 1995. (14) Peria, O., Francois-Joubert, A., Lavallée, S., Champleboux, G., Cinquin, P., Grand, S.: "Accurate Registration of SPECT and MR brain images of patients suffering from epilepsy or tumor," *Proceedings of the First International Symposium on Medical Robotics and Computer Assisted Surgery,* Volume II, Session IV, Pages 58–62, Pittsburgh, Pa., Sep. 22–24, 1995. (15) Lea, J. T., Watkins, D., Mills, A., Peshkin, M. A., Kienzle III, T. C., Stulberg, D. S.: "Registration and Immobilization for Robot-Assisted Orthopaedic Surgery," *Proceedings of the First International Symposium on Medical Robotics and Computer Assisted Surgery,* Volume I, Sessions I–III, Pages 63–68, Pittsburgh, Pa., Sep. 22–24, 1995. (16) Ault, T., Siegel, M. W.: "Frameless Patient Registration Using Ultrasonic Imaging," *Proceedings of the First International Symposium on Medical Robotics and Computer Assisted Surgery,* Volume I, Sessions I–III, Pages 74–81, Pittsburgh, Pa., Sep. 22–24, 1995. (17) Champleboux, G., Lavallée, S., Cinquin, P.: "An Optical Conformer for Radiotherapy Treatment Planning," *Proceedings of the First International Symposium on Medical Robotics and Computer Assisted Surgery,* Volume I, Sessions I–III, Pages 69–73, Pittsburgh, Pa., Sep. 22–24, 1995.

Various systems for image registration using fiducial implants are also described in U.S. Pat. Nos. 4,991,579; 4,945,914; 5,094,241; 5,119,817; 5,097,839; 5,142,930; 5,211,164; 5,230,338; 5,222,499; and 5,397,329 to Allen.

A system and method for performing robotically assisted surgery is described in U.S. Pat. No. 5,086,401. Computer-assisted imaging and probe tracking systems are described in U.S. Pat. Nos. 5,383,454; 5,198,877; and WO 91/07726. Copending and recently allowed application Ser. No. 08/526,826, assigned to the assignee of the present application, describes a method and system for transforming a bone image into a robotic coordinate system by aligning a robotic probe within the medullary canal of the femur. Patent application Ser. No. 09/022,643, also assigned to the assignee of the present application, describes a method and system for transforming a bone image into a robotic coordinate system based upon registering between the robotic coordinate system and the image data set 1) two positional coordinates axially spaced apart along the bone and 2) a directional vector passing through at least one of the positional coordinates.

SUMMARY OF THE INVENTION

According to the present invention, improved methods, systems, and apparatus are provided for registering the image of a bone to a coordinate system, with the bone itself immobilized in the coordinate system, typically a robotic coordinate system of the type used for performing surgical procedures, such as hip replacement surgery, knee replacement surgery, long bone osteotomies, and the like. The improvement avoids the use of fiducial marking pins and comprises registering a bone image data set with the robotic coordinate system as follows. First, a bone image data set is generated by applying various image processing algorithms to a bone image, such as the bone image that would be acquired by a conventional scanner, for example a computerized tomography (CT) scanner. An articulated movable digitizer arm is then used to generate a digitized bone data set comprising coordinates representing the position of a plurality of surface locations on the bone (the digitized bone data set being generated in the robotic coordinate system, as will be explained). Alternatively, the digitized bone data set may be generated by the robotic arm itself. The bone image data set is then transformed into the robotic coordinate system by fitting coordinates of the bone image data set to corresponding coordinates of the digitized bone data set, preferably by a least squares best-fit technique. For the digitizer arm to generate a digitized bone data set in the robotic coordinate system, the coordinate system of the bone digitizer arm is preferably pre-registered to the robotic coordinate system, using a variety of techniques as will be described.

An important advantage of the present invention is the elimination of fiducial marking pins attached to the bone prior to surgery.

The bone image is usually acquired by computerized tomography (CT), digital radiography, or the like. The bone image data set is then generated from the acquired bone image and represents a geometric coordinate model of the surface of the bone. Various image processing methods are able to generate a generalized surface model of the bone, including faceted graphical representation. To obtain the best possible accuracy, the bone image data set must preferably have very high resolution, (ie: very small facets). However, achieving such high resolution presents practical difficulties since if the entire bone surface was modeled to high resolution, the model itself would be extremely large, creating unwieldy computations when transforming this bone image model to the robotic coordinate system. Because such computation must be completed during surgery, it is desirable to minimize the model. Accordingly, surfaces of the bone which are within well defined regions of interest (in particular the distal and proximal ends of the bone), are preferably modeled to a higher degree of resolution.

The bone image data set generated from the bone image preferably includes data representing only the outer surfaces of the bone. This is accomplished both to help reduce the size of the model data set and also to increase robustness of the transformation calculation. If both inner and outer surfaces of the bone were instead also included in the bone image data set, inaccuracies could develop in determining the optimal transformation of the bone image data set to the robotic coordinate system. Accordingly, when generating the bone image data set from the computer tomography bone image, it is preferable to use an interactive threshold function such that it is possible to easily differentiate between bone tissue which is to be included in the data set and surrounding soft tissue which is not to be included in the data set. Thereby, a selectively high resolution representation of operative locations or other locations of interest on the bone surface can readily be generated.

As stated, by avoiding the need for high resolution across the entire surface of the bone, the size of the data set can be somewhat minimized. Accordingly, a very accurate coordinate system transformation can therefore be accomplished without the bone image data set itself becoming so large so as to be cumbersome in calculation. Therefore, a very fast or approximate real time response is possible during surgery.

Prior to, concurrent with, or subsequent to generating the bone image data set from the bone image, an articulated bone digitizer arm preferably having a fixed proximal end and a freely moving distal end is pre-registered to the robotic coordinate system, using a variety of techniques which will be described herein. Subsequent to its registration, the bone digitizer arm is used to generate the digitized bone data set as follows. The bone is first immobilized within the robotic coordinate system and the freely movable distal end of the digitizer arm is then moved to contact the bone surface at a plurality of different locations on the bone. The position of each of these surface locations is thereby determined and recorded thereby forming the digitized bone data set. Since the bone digitizer arm is pre-registered to the robotic coordinate system, the digitized bone data set will also be in the robotic coordinate system.

Alternatively, the digitized bone data set can be gathered using the surgical robotic arm itself. In this aspect of the invention, a freely movable distal end of the surgical robotic arm is then moved to contact the bone surface at a plurality of different locations on the bone. The position of each of these surface locations is thereby determined and recorded thereby forming the digitized bone data set.

In alternative aspects of the invention, a non-contact digitizing apparatus, such as an ultrasound or laser system, can be used to generate the digitized bone data set. In this aspect of the invention, the ultrasound or laser system is used to sense and record the position of a plurality of locations on the surface of the bone.

The digitized bone data set, (which is preferably produced by contacting the freely movable end of the digitizer arm against various locations on the surface of the bone as explained), is preferably generated to comprise data points at the distal and proximal ends of the bone. Accordingly, the digitized bone data set will be selectively more detailed, at the distal and proximal ends of the bone. Such higher data resolution of the digitized bone data set at the ends of the bone is achieved by contacting the digitizer arm to the bone surface at a greater number of points near the ends of the bone as compared to points along the mid-section of the bone.

As such, the coordinate data points of the digitized bone data set will correspond to the high resolution regions of the bone image data set, thereby ensuring an optimal transformation calculation. An additional advantage of generating the digitized bone data set to comprise data points at only the opposite ends of the bone is that it is therefore not necessary to surgically access mid-portions of the bone to acquire surface data points. As such, surgical trauma to the patient is substantially reduced.

In a preferred aspect of the invention, the digitizer arm comprises an articulated linkage having high resolution position sensors at each joint. The proximal end of the digitizer arm remains fixed at a known location in the robotic coordinate system. Using an embedded processor and appropriate software, the digitizing arm can produce an accurate measurement of the position of its distal tip relative to its base. Preferably as well, when generating the digitized bone data set, the distal end of the digitizer arm is tipped with a sterile probe. It is to be understood, however, that the system for generating the digitized bone data set of the present invention is not limited to an articulated linkage. For example, in contrast to an articulated digitizer arm, the digitized bone data set could be produced by optical sensors, (such as the OPTOTRACK™ system, produced by Northern Digital of Waterloo, Ontario, Canada), ultrasound, or lasers.

As was stated, the digitized bone data set represents the locations of a plurality of points on the surface of the bone in the robotic coordinate system, as determined by the digitizer arm. In the case of a femur bone, the digitized bone data set preferably includes medial, anterior, and lateral surface locations on a distal end of the femur, a plurality of surface location points at the proximal end of the femur, including points around the neck of the femur, and a point at the top proximal end of the femur. From these various surface location points, distal and proximal end centroids can be calculated for the femur.

The generated digitized bone data set may itself may be verified by comparison to a standard bone image surface model. Specifically, the coordinates representing the various surface locations of the bone image data set can be compared against a standard bone image coordinate model, (ie: a standard bone shape model), to determine whether variations in spatial relation among such surface locations are within expected tolerances. Should coordinates of the digitized bone data set exceed expected tolerances from a standard bone model shape, (thus indicating data representative of an odd-shaped bone), this would seem to suggest errors in initial collection of the coordinate points of the digitized bone data set, such that the user should be prompted to re-generate the digitized bone data set by again contacting the distal end of the digitizer arm against various preferred locations on the surface of the bone.

Subsequent to the generation of the bone image data set, (which is not in the robotic coordinate system), and the digitized bone data set, (which is in the robotic coordinate system), the present invention provides a system for transforming the bone image data set into the robotic coordinate system by performing a best fit calculation between coordinates of the bone image data set and corresponding coordinates of the digitized bone data set. Specifically, the various surface location coordinates of the digitized arm data set are used to transform the bone image into the robotic coordinate system by way of a best-fit calculation which preferably comprises minimizing the sum of the squares of the distances between the coordinates of the bone image data set and the corresponding coordinates of the digitized bone data set. Specifically, the distances between the coordinates of the bone image data set (which is treated as a rigid body) and the digitized bone data set (which is also treated as a rigid body) is minimized. This best fit procedure is preferably performed as an iterative calculation which may preferably use a first comparison of the relative positions of an end of the bone, and of the distal and proximal centroids of the bone as calculated from the bone image data set compared with those as calculated from the digitized bone data set. The position and orientation of a "cut cavity" coordinate system, which represents the region of bone to be milled away by a surgical robotic arm, can then be superimposed on the transformed bone image data set, such that the position of the surgical robotic arm relative to the bone can be established and controlled.

The best-fit calculation can itself be verified by a number of different techniques including determining the mean distances between the coordinates of the transformed bone image data set and the digitized bone data set. Alternatively, verification can be achieved by determining the number of coordinates of the transformed bone image data set that are more than a threshold distance away from corresponding coordinates of the digitized bone data set. Finally, verification can also be achieved by comparing the distance from the furthest coordinate of the transformed bone image data set to the position of its corresponding coordinate in the digitized bone data set.

In another aspect of the present invention, the bone digitizer arm is pre-registered to the robotic coordinate system, as follows. A digitizer arm test data set is generated comprising the position of a plurality of test structures on a test fixture, as measured by the digitizer arm. This digitizer arm test data set is then compared to the actual pre-measured positions of the test structures on the test fixture to verify the measurement accuracy of the digitizer arm. A similar procedure is carried out with the surgical robotic arm with the same test fixture. Specifically, the surgical robotic arm is registered to the robotic coordinate system by first generating a surgical robotic arm test data set comprising the positions of each of the plurality of test structures on the test fixture, this time as measured by the robotic arm. The robotic arm test data set is then compared to the actual pre-measured positions of the test structures on the test fixture to similarly verify the measurement accuracy of the surgical robotic arm.

Having determined the measurement accuracy of both the bone digitizer arm and the surgical robotic arm with respect to a fixed set of coordinates, it is then possible to generate a transformational relationship directly between the bone digitizer arm and the surgical robotic arm. Accordingly, it is then possible to guide the surgical robotic arm as it operates on the bone, based upon positional information initially provided by the bone digitizer arm, with the digitizer arm and the surgical robotic arm both being registered to the same robotic coordinate system.

Accordingly, hip replacement surgery may be performed by positioning the surgical robotic arm based on information in a transformed image data set obtained by any of the methods described above. The surgical robotic arm is positioned according to a preoperative plan, and the robotic cutter, attached thereto, is actuated and manipulated to produce a cavity in the femur for receiving a hip joint prosthesis. The hip joint prosthesis is implanted within the cavity in a generally conventional manner.

The present invention still further provides an improved robotic system which includes a programmable controller which positions the cutter within a robotic coordinate system. A bone image data set representing the image of a long bone is transformed to the robotic coordinate system to permit the controller to position the cutter according to a predetermined operative plan.

The present invention still further comprises a controller program for the robotic system of the type described above. The controller program comprises an instruction algorithm embodied in a tangible medium which performs the best-fit calculation between coordinates of the bone image data set and corresponding coordinates of the digitized bone data set. The algorithm itself may be embodied in any conventional medium of the type used to program controllers and computers, including disks, read only memory, random access memory, flash memory, tapes, CD Rom, and the like.

Optionally, in further aspects of the present invention, additional positioning markers can be attached directly to the bone to thereby enable bone motion to be continuously or periodically monitored and corrected during surgery, with the position of these optional positioning markers being monitored over time by the bone digitizer arm.

The methods, systems, and apparatus of the present invention are particularly advantageous since they provide for very accurate registration of the bone image data set to the actual bone position when immobilized in the coordinate system. Such close tolerances allow for positioning of hip joint implants with very good initial mechanical stability and excellent tissue ingrowth.

DESCRIPTION OF THE PREFERRED EMBODIMENT

The present invention is intended for registering the image of the long bone with the long bone itself immobilized within a system coordinate space. Long bones which may be imaged and registered include the femur, tibia, humerus, ulna, and radius. Image registration of such long bones will be particularly useful in conjunction with robotic surgical procedures, such as joint replacement, with specific procedures including total hip joint replacement, knee joint replacement, long bone osteotomy, and the like. Exemplary methods, systems, and apparatus for transforming an image data set of the femur within a robotic system intended for performing total hip replacement surgery are described hereinafter, but such descriptions are not intended to be limiting to the scope of the present invention.

The present invention provides methods, systems, apparatus for transforming a bone image data set representing the geometric shape of the long bone into a system coordinate space, typically a robotic system intended to perform or assist in any of the procedures described above. The present invention, however, is not limited to such robotic procedures and will be equally useful in manual surgical, diagnostic, and other medical procedures where it is necessary to align a pre-obtained image of a long bone within an actual coordinate space, such as an operative space. Such manual systems and procedures include computer-assisted surgical procedures that employ optical surgical measurement tools, passive electromechanical devices, and the like. In such cases, the use of the present invention is advantageous in that it will provide highly accurate image registration with an immobilized long bone without the need to preimplant multiple fiducial markers along the bone and/or surgically access the bone at multiple points along its length.

The present invention relies on first obtaining an image of the bone using a conventional medical imaging technique, such as computerized tomography (CT), radiography (digitized X-ray images), magnetic resonance imaging (MRI), and the like. Usually, CT and radiographic imaging will be preferred since they provide particularly accurate imaging information of bone material. In all cases, the image will be obtained in or converted to a digital form to produce a bone image data set which is suitable for digital manipulation using conventional computerized image processing equipment and software. Usually, the image processing equipment will be in the form of specially programmed computers, which are generally referred to as controllers and processors hereinafter. In particular, the present invention will utilize a preoperative planning workstation (computer) for analyzing and manipulating the bone image data set which is obtained directly from the image itself.

The bone image data set is generated from the bone image and represents a geometric coordinate model of the outer surface of the bone. As the bone image is preferably obtained prior to surgery, the resultant bone image data set corresponding thereto needs to be transformed into the robotic coordinate system immediately prior to surgery. The present invention provides systems for accomplishing this transformation based upon first obtaining a digitized bone data set comprising bone surface location coordinates in the robotic coordinate system, as generated by contacting a bone digitizer arm against various locations on the bone prior to surgery. The bone image data set is then transformed into the robotic coordinate system by fitting the bone image data set to the coordinates of the digitized bone data set, as will be explained.

Returning to the bone image data set, the degree of resolution of this bone image data set is preferably much higher at specific locations on the bone, preferably being the distal and proximal ends of the bone. The bone image data set can be generated with the user first determining the preferred areas of high resolution on the bone. Alternatively, the pre-operative planning workstation could be programmed to identify such suitable high resolution locations without specific user intervention. In either case, the bone image data set will be subsequently transferred to the operative or other system where the bone is to be immobilized.

Figure 1:
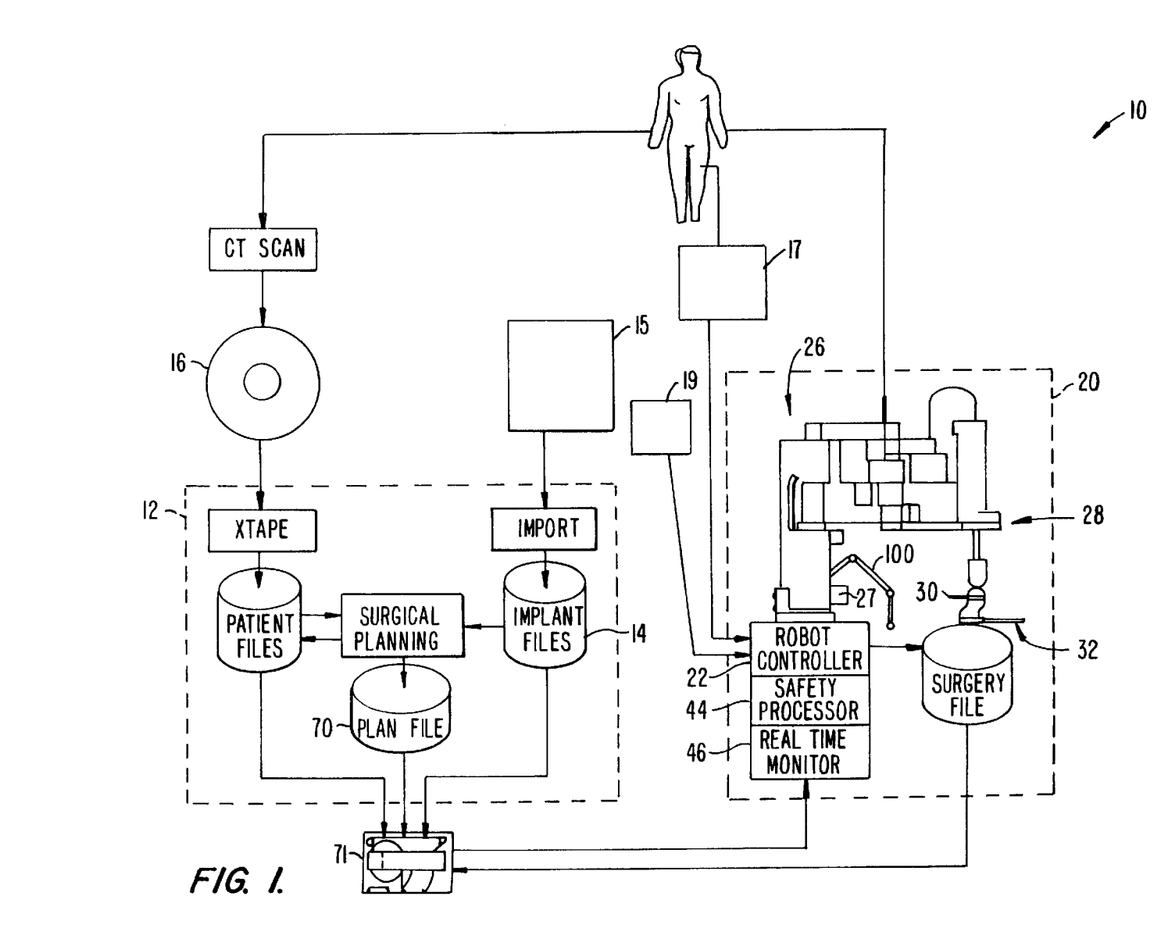
FIG. 1 illustrates the architecture of a robotic surgical system according to the present invention. The system includes a presurgical planning component and a surgical component.

Referring to the Figures, an exemplary system 10 capable of implementing the methods of the present invention for hip replacement surgery is illustrated in FIG. 1. The system 10 includes both a presurgical planning workstation 12 and a library of implant designs 14 in the form of CAD model data sets 15. A bone image data set 16, typically representative of a CT bone image, is obtained and transferred into the presurgical planning workstation 12. The user, typically the treating physician or an assistant working with the treating physician, is able to work at the presurgical planning workstation to select and position a suitable implant design within the patient femur. Details of such presurgical planning are well described in the literature relating to the ORTHODOC™ presurgical planning system cited above.

Figure 2:
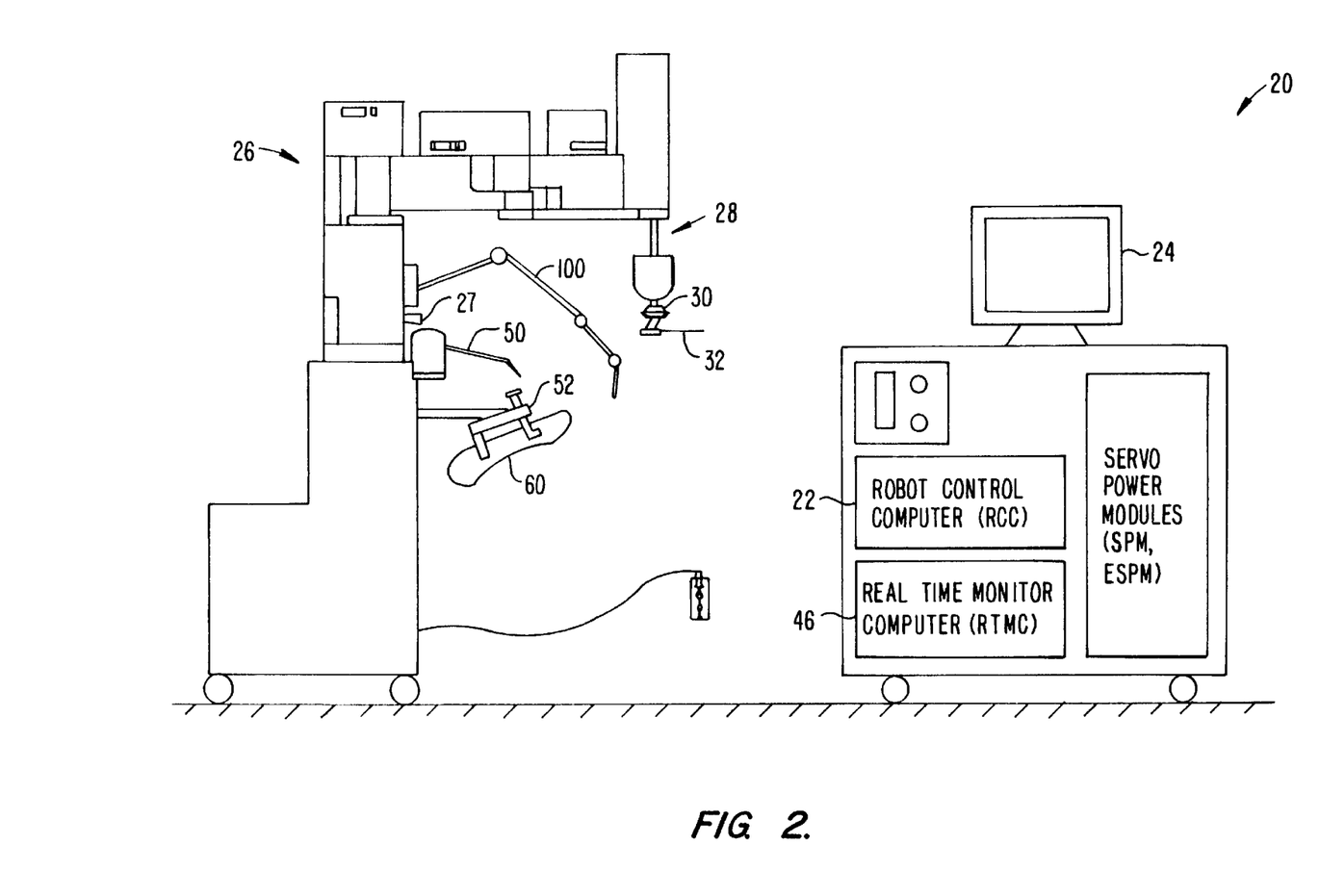
FIG. 2 illustrates the surgical component of the surgical system of FIG. 1 and includes the surgical robot with its associated controller, tooling, and safety interlocks, a bone digitizer arm having a sterile tipped probe, a fixator to hold the bone securely to the robot, a bone motion detector, a human-machine interface with online display computer, and a hand-held terminal interfaced to the robot controller.

The system 10 of the present invention further comprises a robotic operative system 20 which includes a robotic controller 22 (typically a digital processor in the form of a programmable computer), an online display screen 24, and a robot 26. Details of the robotic operating system 20 are shown in FIG. 2. The robot can be any conventional industrial robot having a manipulatable surgical robotic arm 28 preferably having at least 5 axes and capable of high precision placement. A suitable surgical robotic is available from Sankyo Robotics with the model designation SR-5427-ISS. For use in the present invention, a force sensor 30 is mounted at the distal end of arm 28, and an effector in the form of a probe 32 or a surgical cutting tool (not illustrated) may be attached to the force sensor.

The robotic system 20 further includes a safety processor 44, and a real time monitoring computer 46, as illustrated in FIG. 1. The force sensor 30, the safety processor 44, the real time monitor 46, and a bone motion monitor 50, each help monitor the position, slippage, and blockage of the effector end of the manipulatable arm 28 while the femur 60 is held in place in a fixator assembly 52. Real time monitoring of these parameters helps assure that the robotic system is operating as planned. Details of these monitoring systems are described in the literature cited above which describes the ROBODOC™ robotic surgical system.

Figure 3:
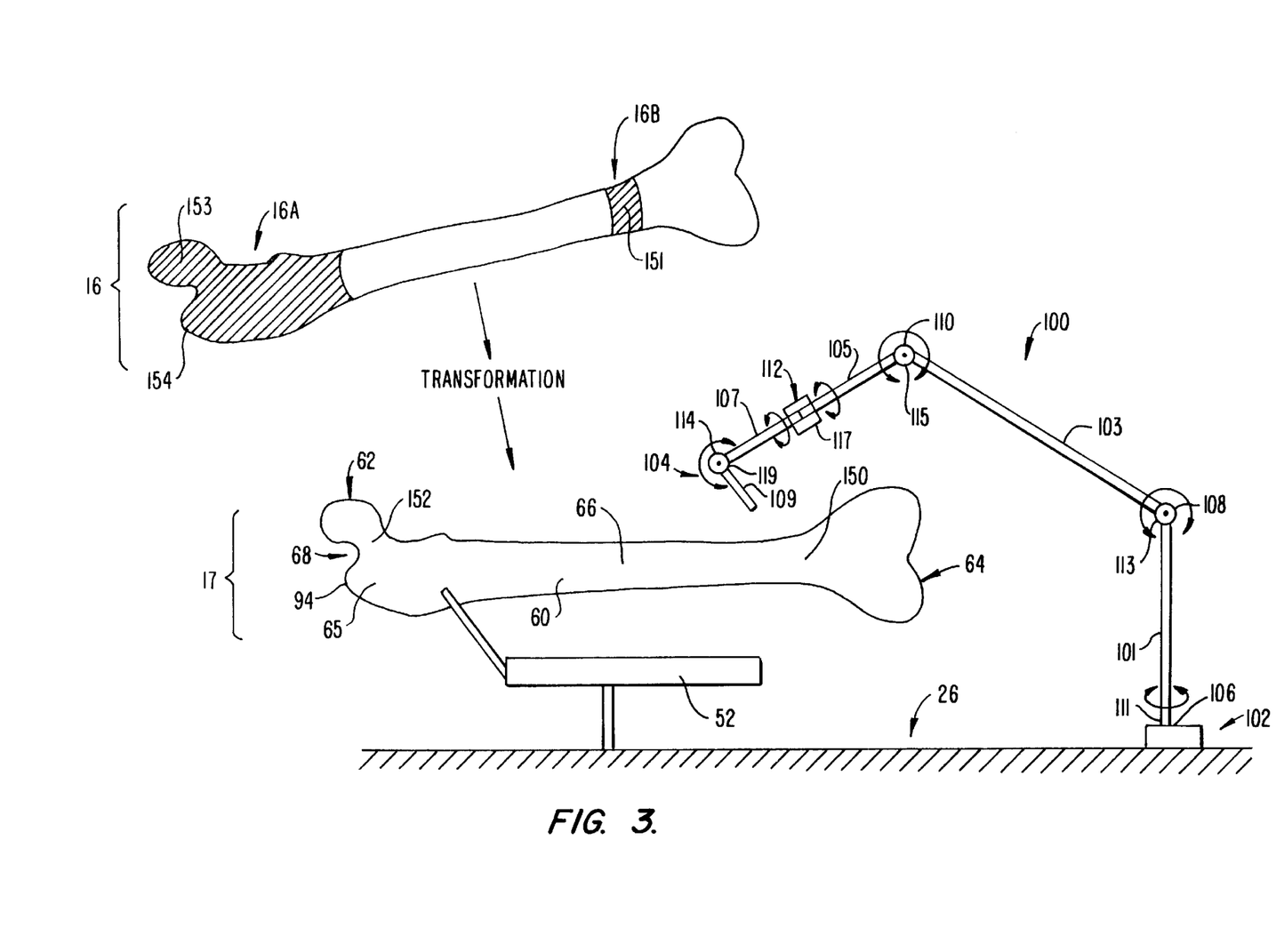
FIG. 3 is a schematic illustration of the transformation of the bone image data set into a robotic coordinate system, showing structural details of the bone digitizer arm and its manner of use on a human femur.
Figure 5:
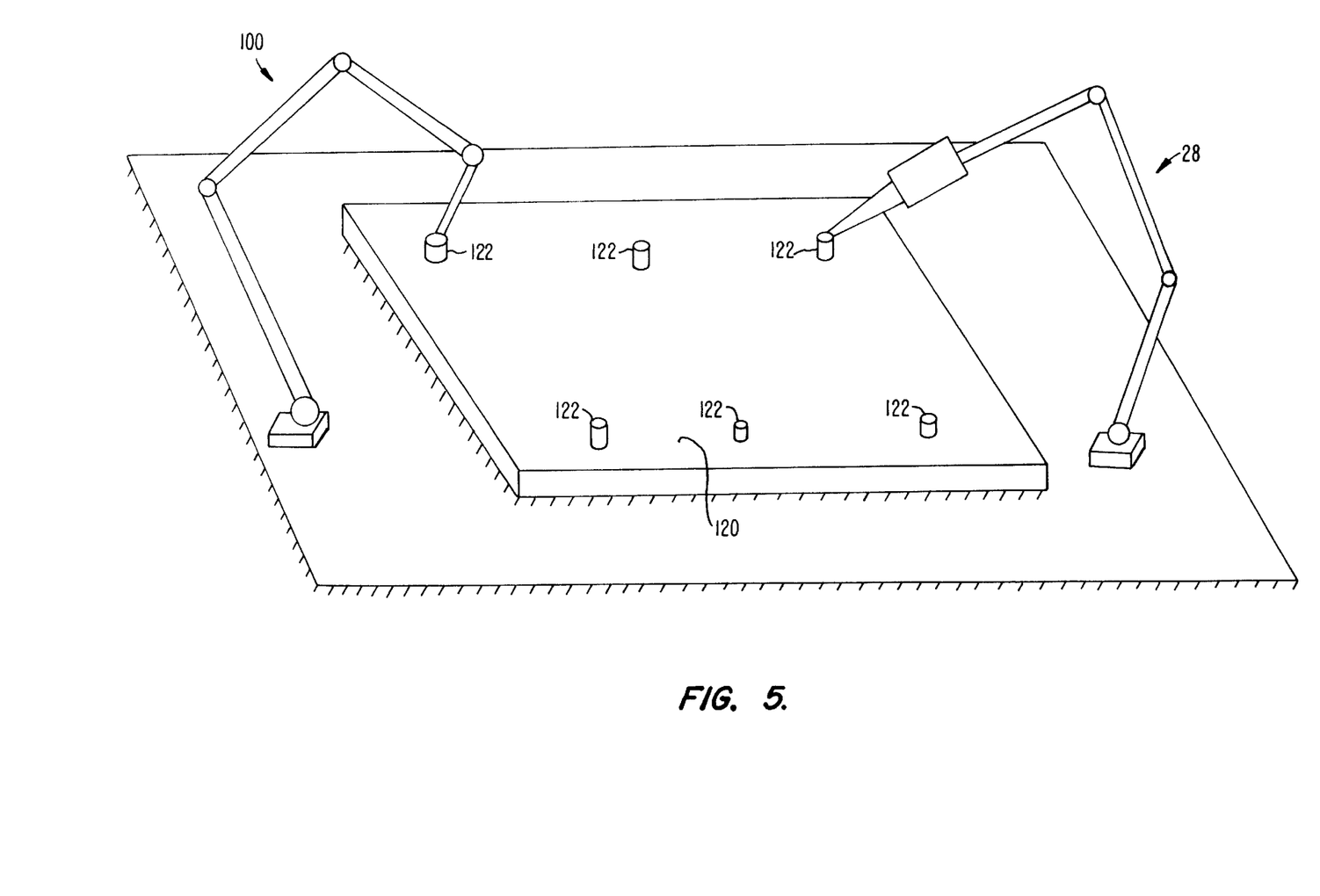
FIG. 5 is a schematic illustration of the use of a test fixture to pre-register each of the bone digitizer arm and a surgical robotic arm to the robotic coordinate system.

As stated above, the present invention relies upon obtaining a digitized bone data set which comprises the coordinate positions of a number of surface locations on the bone as measured by a bone digitizer arm registered to the robotic coordinate system. Accordingly, system 10 further includes bone digitizer arm 100, the details of which are best shown in FIGS. 3 and 5. As will be explained, an acquired digitized bone data set 17, (shown in FIG. 1 as an input to robotic controller 22), is obtained by bone digitizer arm 100 and is used to transform bone image data set 16 into the robotic coordinate system.

Referring to FIG. 3, fixator assembly 52 is first used to immobilize proximal end 62 of femur 60. Being attached to robot 26, fixator assembly 52 will immobilize femur 60 within the robotic coordinate system. Femur 60 comprises a head (proximal) region 62 and a lower (distal) region 64. The trabecular bone 65 that is located adjacent the femoral head 62 and the cortical bone 66 is located generally between the two ends of the bone. A neck region 68 is located just below the femoral head above the trabecular bone.

Bone digitizer arm 100 is preferably an articulated structure having a fixed proximal end 102 and a freely movable distal end 104, as shown. Being attached to robot 26, its fixed proximal end 102 will be immobilized at a known location within the robotic coordinate system. Digitizer arm 100 preferably is comprised of a plurality of links 101, 103, 105, 107 and 109, connected at joints 106, 108, 110, 112 and 114, as shown. High resolution position sensors 111, 113, 115, 117 and 119 are disposed at flexible joints 106, 108, 110, 112, and 114 as shown. Using position sensors 111, 113, 115, 117, and 119 and appropriate software, bone digitizer arm 100 can produce accurate measurements of the position of distal end 104, (and specifically the sterile tipped probe link 109 mounted thereto), with respect to fixed proximal end 102 as distal end 104 is moved to various locations. As can be seen schematically in FIG. 3, rotation about flexible joints 106, 108, 110, 112, and 114 is accomplished with various joints rotating about axes normal to one another such that motion of distal end 104 of digitizer arm 100 can be accomplished in any of 5 degrees of freedom relative to fixed distal end 102.

Digitized bone data set 17 is generated by contacting sterile tipped probe link 109 against a plurality of surface locations on the surface of the bone, while recording these locations as a set of positional coordinates. (These locations preferably include, for example, locations 80, 81, 82, 83, 84, 85, 86, 87, 88, 89, 90, 91, 92, 93, 94, 95, 96 and 97 as best seen in FIGS. 4A, 4B, 4C and 4D, as will be explained). Since the position of proximal end 102 is initially at a known location in the robotic coordinate system, the positions of each of the coordinates of digitized bone data set 17 will also be determined in the robotic coordinate system.

In alternative aspects of the present invention, the digitized bone data set is generated by robotic arm 28. In this aspect of the invention, the movable distal end of the surgical robotic arm is moved to contact the bone surface at a plurality of different locations on the bone, (similar to the above described approach in which the digitized bone data set was gathered by digitizer arm 100. The position of each of these surface locations is thereby determined and recorded thereby forming the digitized bone data set.

In alternative aspects of the invention, a non-contact digitizing apparatus, such as an ultrasound or laser system 27, can be used to generate the digitized bone data set. In this aspect of the invention, the ultrasound or laser system is used to sense and record the position of a plurality of locations on the surface of the bone.

The detected position of the coordinates comprising digitized bone data set 17 are then used to transform bone image data set 16 into the robotic coordinate system, as will be explained. For schematic illustration purposes and for ease of understanding, bone image data set 16 is simply shown as an image of the bone floating in space above immobilized femur 60. (This is because, prior to transformation, the exact position of bone image data set 16 is not known within the robotic coordinate system.) For illustration purposes, the transformation of bone image data set 16 into the robotic coordinate system is understood to correspond to moving bone image data set 16 such that its coordinates become superimposed on femur 60.

For ease of understanding, bone image data set 16 is shown as corresponding to the entire surface shape of the femur. It is to be understood, however, that bone image data set 16 need preferably only comprise high resolution data regions corresponding to opposite ends 16A and 16B of the bone.

Referring to FIGS. 4A, 4B, 4C and 4D, the preferred coordinates selected to comprise digitized bone data set 17 can be seen. These preferred coordinates are selected to correspond to coordinate locations in bone image data set 16. In particular, the coordinate locations of digitized bone data set 17 are all preferably near the opposite ends of the femur, as shown. The coordinate locations of digitized bone data set 17 are preferably collected by the operator manually contacting sterile tipped probe link 109 against the surface of bone 60 at each of locations 80, 81, 82, 83, 84, 85, 86, 87, 88, 89, 90, 91, 92, 93, 94, 95, 96 and 97. The positions of each of these locations, with respect to the position of proximal end 102 will thus be identified and recorded as digitized bone data set 17.

As can be seen, digitized bone data set 17 preferably includes the coordinate positions of medial 80, lateral 81, and anterior 82 locations at the distal end 64 of the femur. From locations 80, 81, and 82, the location of a distal end centroid 150 can be calculated. Digitized bone data set 17 preferable also includes the positions of a plurality of surface locations 83 to 96 around and near neck 68 of proximal end 62 of the femur. From surface locations 83 to 92, the location of a proximal end centroid 152 can be calculated. In addition, the location of the top end 97 of the femur is also preferably added to digitized bone data set 17.

Figure 4A:
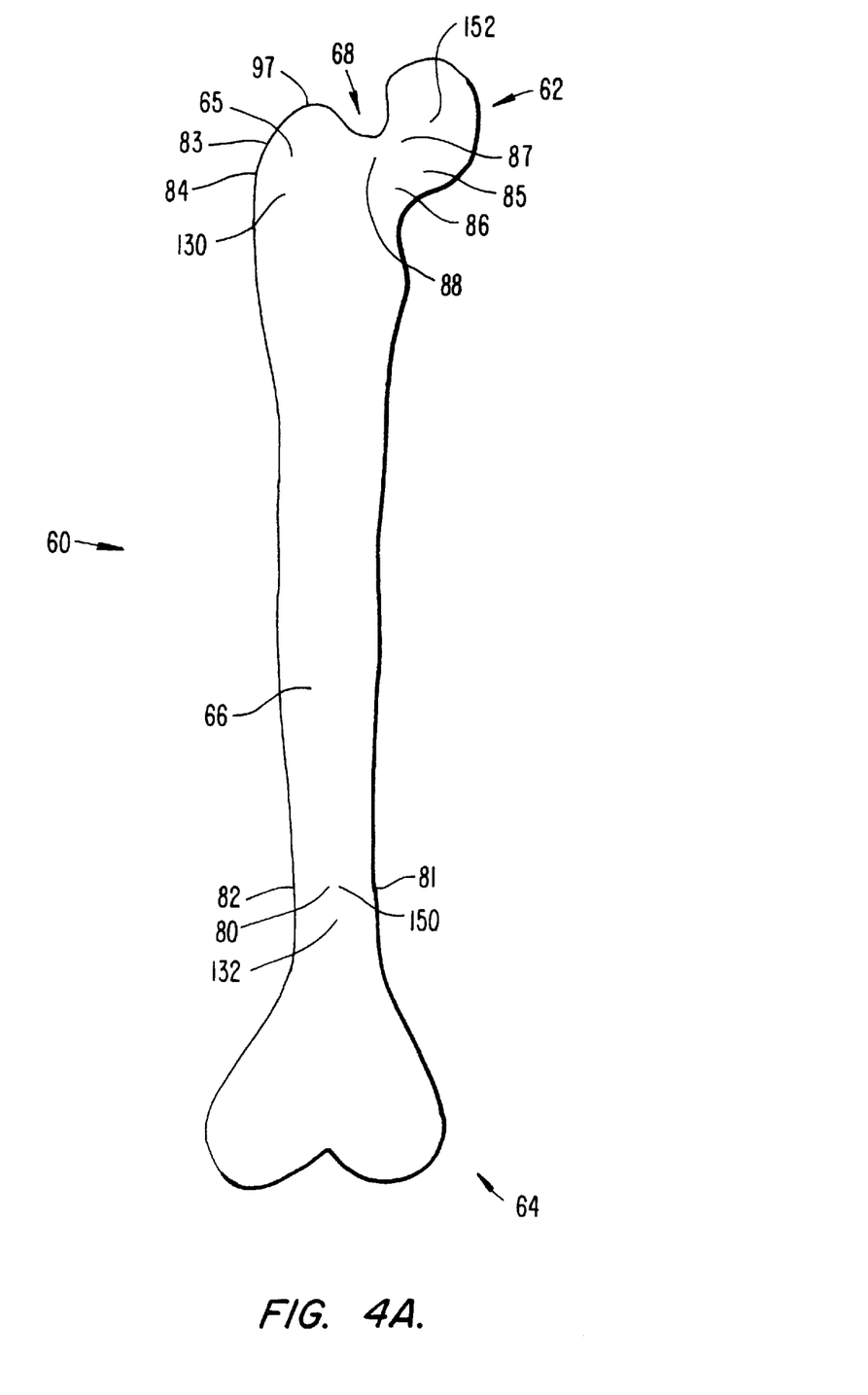
FIG. 4A is an enlarged anterior-posterior view of the femur of FIG. 3, showing surface contact locations for generating the digitized bone data set.
Figure 4B:
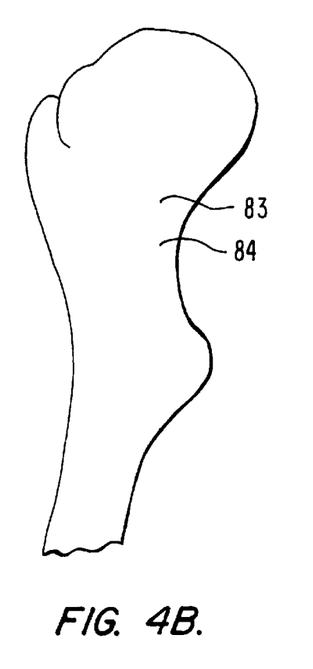
FIG. 4B is a medial-lateral view of the proximal end of the femur of FIG. 4A.
Figure 4C:
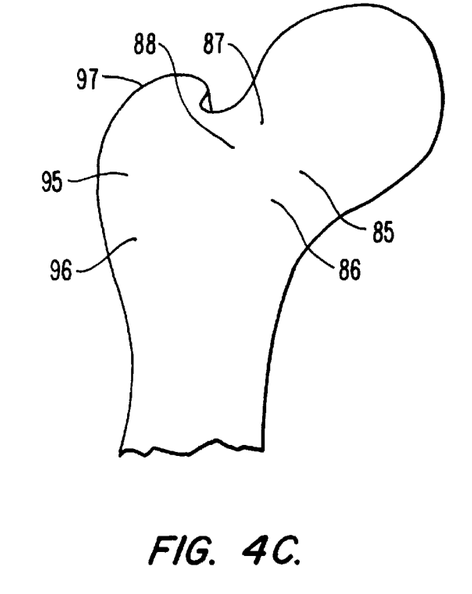
FIG. 4C is an anterior-posterior view of the proximal end of the femur of FIG. 4A.
Figure 4D:
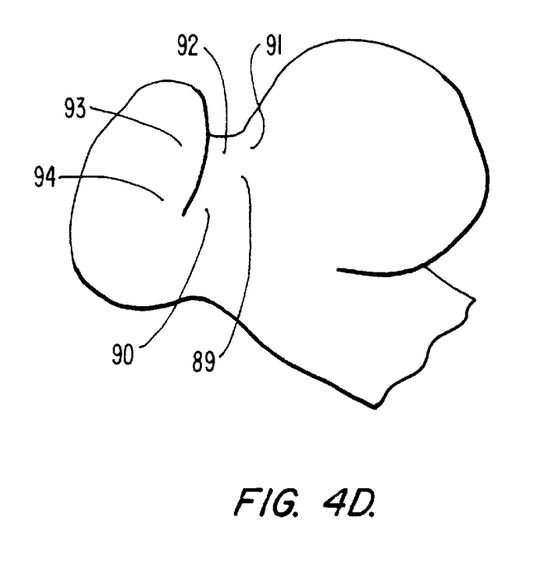
FIG. 4D is a perspective view of the proximal end of the femur of FIG. 4A.

The collection of data point locations 80, 81 and 82 at distal end 64 of the femur can preferably be accomplished percutaneously through the soft tissue by way of a sterile tipped probe at the distal end of link 109. Accordingly, when collecting data in this manner, it is not necessary to expose the distal end of the femur during surgery. When collecting data points at locations 83 to 97, at proximal end 62 of the femur, proximal end 62 of the femur will already be exposed during surgery, thus enabling the operator to easily directly contact bone surface locations 83 to 97, around and adjacent neck 68 of the femur. During the collection of data point locations at either of the distal and proximal ends of the femur, graphical display 24 will preferably assist in guiding the user to the correct locations.

A standard bone surface model file 19 representing a typical or standard geometric bone shape, can also be stored in robotic controller 22 and can be used for verifying digitized bone data set 17. Specifically, each of the coordinates of digitized bone data set 17 can be compared to standard bone surface model file 19 such that the likelihood of digitized bone data set 17 being an unacceptable representation of the shape of the bone can be determined. Should the coordinates of digitized bone data set 17 appear to stray from accepted tolerances, this would suggest an error in gathering the data set and the user could then be prompted to re-gather the data by re-positioning distal end 104 of bone digitizer arm 100 to re-determine correct positions of location coordinates 80 to 97.

Figure 4E:
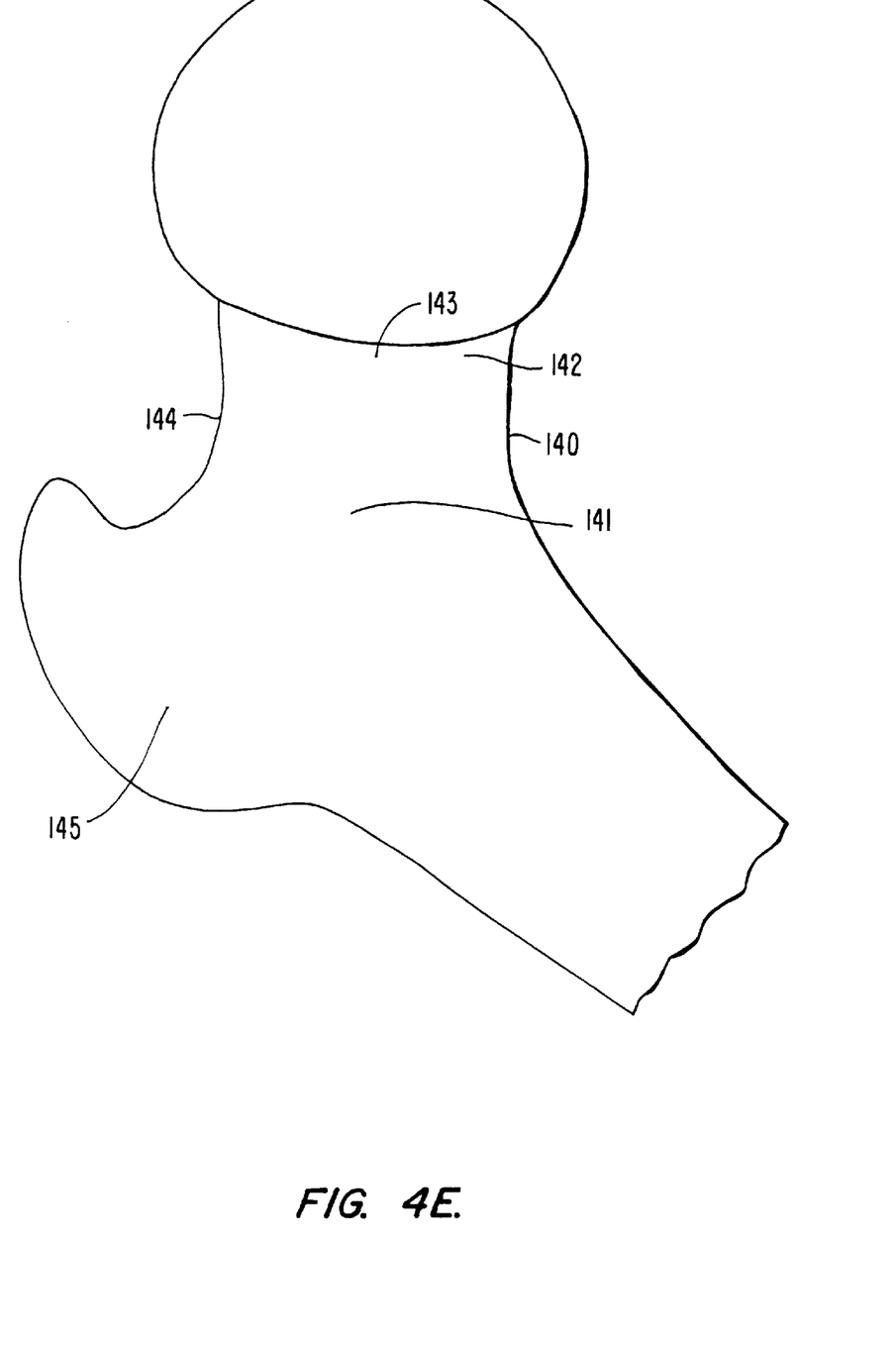
FIG. 4E is a view corresponding to FIG. 4C, but showing post-transformation digitized coordinates.

Optionally, in addition to mathematically verifying digitized bone data set 17, the user also preferably performs a visual check of the transformation correctness by digitizing additional bone surface locations including 140, 141, 142, 143, 144, and 145, as seen in FIG. 4E, and re-digitizing bone surface locations at points 80 and 81 of FIG. 4A. Bone surface locations 140 to 145 (and re-digitized locations 80 and 81) are preferably selected to identify translation or rotational errors in any of the six possible degrees of freedom. As each additional location 140 to 145, 80 and 81, is digitized, it is transformed from the robotic coordinate system to the bone image coordinate system (using the inverse transformation of the previously used best-fit transformation which transformed the digitized bone data set into the robotic coordinate system) such that locations 140 to 145, 80 and 81 are displayed on top of the bone image data set on display 24. Since these newly digitized points are physically on the bone surface, the displayed points corresponding thereto should also appear superimposed at the bone surface in an on screen bone image.

As stated, the present invention transforms the bone data image data set 16 into the robotic coordinate system by fitting the bone image data set 16 to corresponding coordinates found in the digitized bone data set 17 by way of a best-fit calculation. Such best-fit calculation may preferably be carried out within robot controller 22 with a data transfer file 70 comprising bone image data set 16, implant shape data and implant placement data. Robot controller 22 also receives as input data the digitized bone data set 17, and standard bone surface model file 19. Data transfer file 70 is typically transferred to robot controller 22 through interface 71 which may comprise data transmission lines, data transfer tape, or any other conventional data transfer system.

In a preferred aspect of the present invention, the sum of the squares of the distances between the coordinates of bone image data set 16 and digitized bone data set 17 are minimized. Referring to FIG. 3, this best-fit calculation may be carried out as an iterative solution which commences from a first comparison of the relative positions of: end 97, distal end centroid 150 and proximal end centroid 152 of bone 60, as calculated from digitized bone data set 17 with end 154, distal end centroid 151 and proximal end centroid 153 of bone 60, as calculated from bone image data set 16. Subsequently, a "cut cavity" coordinate system, (which represents the bone to be milled away by a cutting device on surgical robotic arm 28), can then be superimposed on the transformed bone image data set 16 for controlling the milling of the bone by the surgical robotic cutting arm.

The bone digitizer arm 100 is pre-registered to the robotic coordinate system such that the collection of coordinate data comprising digitized bone data set 17 will also be in the robotic coordinate system, as follows. Referring to FIG. 5, bone digitizer arm 100 is registered to the robotic coordinate system by first generating a digitizer arm test data set representing the position of a plurality of test structures 122 on a test fixture 120 with bone digitizer arm 100. Subsequently, a similar procedure is repeated for robotic arm 28 wherein the a robotic arm test data set is generated representing the position of the test structures 122 on test fixture 120, this time as determined by the robotic arm. The exact pre-measured locations of each of test structures 122 on test fixture 120 will already be known.

Test fixture 120, proximal end 102 of digitizer arm 100, and the base of surgical robotic arm 28 are all securely affixed to a common structure, (for example, robot 26), such that relative motion among these components is prevented. Accordingly, by comparing the digitizer arm test data set with the actual pre-measured positions of the test structures on the test fixture, the positional measurement accuracy of the digitizer arm can be verified. Similarly, by comparing the robotic arm test data set with the actual pre-measured positions of the test structures on the test fixture, the positional measurement accuracy of the robotic test arm can be verified. By comparing the digitizer arm test data set with the robotic arm test data set, a transform relationship can be calculated between measurements taken by the digitizer arm and measurements taken by the robotic arm, thereby accounting for kinematic measurement inaccuracies in both the bone digitizer arm and the surgical robotic arm and thereby registering the digitizer arm to the robotic coordinate system. It is then possible to guide the surgical robotic arm as it operates on the bone, based upon positional information initially provided by the bone digitizer arm, with the digitizer arm and the surgical robotic arm both operating in the same robotic coordinate system.

In another aspect of the present invention, optional marker pins 130 and 132 can be installed in femur 60, (preferably at proximal end 62 and distal end 64, as shown). Bone digitizer arm 100 can then be operated to detect any motion of marker pins 130 and 132 during surgery by continuously or periodically digitizing the locations of pins 130 and 132 by repeatedly contacting sterile tipped probe link 109 against these marker pins. Any movement of marker pins 130 and 132 within the robotic coordinate system will thus be detected by bone digitizing arm 100 such that any unwanted bone motion can be detected and compensated for during surgery. Alternatively, the motion of marker pins 130 and 132 can be tracked by way of a device other than bone digitizing arm 100 such as an additional bone motion detector which may comprise separate flexible mechanical arm, or a laser or ultrasound system.

When only one marker pin (130 or 132) is used, it is possible to detect whether bone movement in one or more of three mutually perpendicular axes has occurred. When two marker pins (130 and 132) are simultaneously tracked over time, however, it is possible to detect rotational movement about the three mutually perpendicular axes such that the precise direction and amount of bone motion can be measured. Accordingly, when using two marker pins, the amount and direction of bone motion detected can be used to update the position of the bone in the robotic coordinate system such that the position of the surgical robotic arm can be guided based upon the current position of the bone within the robotic coordinate system based on the bone motion detected.

What is claimed is:

1. A method for transforming a bone image data set representing at least a partial image of a long bone to a robotic coordinate system, comprising:

providing a bone image data set comprising coordinates corresponding to a bone image;

registering a bone digitizer arm to the robotic coordinate system, said digitizer arm having a plurality of position sensors;

positioning the digitizer arm relative to points on the surface of the bone to generate a digitized bone data set comprising coordinates corresponding to the points; and performing a best-fit calculation between coordinates of the bone image data set and corresponding coordinates of the digitized bone data set to transform the bone image data set into the robotic coordinate system.

2. The method of claim 1, wherein the bone image is provided by computerized tomography.

3. The method of claim 1, wherein the bone image data set has higher resolution at distal and proximal ends of the bone.

4. The method of claim 1, wherein the bone image data set represents coordinates on an outer surface of the bone.

5. The method of claim 4, wherein a threshold determination is made such that the bone image data set includes only bone tissue and excludes soft tissue.

6. The method of claim 1, wherein the bone digitizer arm is registered to the robotic coordinate system by:

positioning the digitizer arm relative to test structures on a test fixture to generate a digitizer arm test data set comprising coordinates corresponding to the locations of the test structures;

positioning a robotic arm relative to the test structures on the test fixture to generate a robotic arm test data set comprising coordinates corresponding to the locations of the test structures; and calculating a transform relationship between the digitizer arm test data set and the robotic arm test data set.

7. The method of claim 1, wherein the accuracy of the bone digitizer arm is verified by:

positioning the digitizer arm relative to test structures on a test fixture to generate a digitizer arm test data set comprising coordinates corresponding to the locations of the test structures; and comparing the digitizer arm test data set to the actual positions of the test structures on the text fixture.

8. The method of claim 1, wherein the accuracy of the robotic arm is verified by:

positioning a robotic arm relative to test structures on a test fixture to generate a robotic arm test data set comprising coordinates corresponding to the locations of the test structures; and comparing the robotic arm test data set to the actual positions of the test structures on the text fixture.

9. The method of claim 1, wherein generating the bone surface data comprises:

selecting a bone digitizer arm having an articulated linkage with a fixed proximal end and a movable distal end;

contacting the distal end of the digitizer arm against the plurality of points on an outer surface of the bone; and recording the position of the plurality of points relative to the proximal end of the bone digitizer arm.

10. The method of claim 9, wherein the plurality of points on the surface of the bone comprises:

medial, anterior and lateral points on a distal end of a femur bone.

11. The method of claim 10, wherein the medial, anterior and lateral points are obtained by percutaneously contacting a thin probe mounted at the distal end of the digitizer arm with the surface of the femur bone.

12. The method of claim 9, wherein the plurality of points on the surface of the bone comprises:

a plurality of points around and adjacent to a neck of a proximal end of a femur bone.

13. The method of claim 9, wherein the plurality of points on the surface of the bone comprises:

a point at a top proximal end of a femur bone.

14. The method of claim 1, wherein the best-fit calculation comprises minimizing the sum of the squares of the distances between the coordinates of the bone image data set and the corresponding coordinates of the digitized bone data set.

15. The method of claim 14, wherein the best-fit calculation is an iterative solution which commences from a first comparison of the relative positions of:

an end of the bone;

a distal end centroid of the bone; and a proximal end centroid of the bone, as calculated from the bone image data set with that as calculated from the digitized bone data set.

16. The method of claim 15, wherein the distal end centroid of the bone data set is calculated from the digitized bone data set coordinates comprising medial, anterior and lateral locations on a distal end of the bone.

17. The method of claim 15, wherein the proximal centroid of the bone is calculated from the digitized bone data set coordinates around a neck of a proximal end of the bone.

18. The method of claim 1, wherein the suitability of the digitized bone data set is determined by comparing the spatial relationship among the coordinates of the digitized bone data set to a spatial relationship among corresponding coordinates in a standard bone image data set.

19. The method of claim 1, wherein the best-fit calculation is verified by determining the mean distance of the coordinates of the transformed bone image data set with respect to corresponding coordinates of the digitized bone data set.

20. The method of claim 1, wherein the best-fit calculation is verified by determining the number of coordinates of the transformed bone image data set that are more than a threshold distance from the corresponding coordinates of the digitized bone data set.

21. The method of claim 1, wherein the best-fit calculation is verified by determining the distance from the furthest coordinate of the transformed bone image data set to a corresponding coordinate of the digitized bone data set.

22. The method of claim 1, further comprising:

subsequently to transforming the bone image data set into the robotic coordinate system, positioning the digitizer arm relative to additional points on the surface of the bone, thereby acquiring additional digitized points; and visually displaying the coordinates of the additional digitized points and the bone image on top of one another.

23. The method of claim 1, further comprising:

attaching two positioning markers to the bone; and at separate intervals of time, determining the position of each positioning marker with the digitizer arm, thereby determining bone motion over time.

24. A method for transforming a bone image data set representing at least a partial image of a long bone to a robotic coordinate system, comprising:

providing a bone image data set comprising coordinates corresponding to a bone image;

positioning a surgical robotic arm relative to points on the surface of the bone said arm having a plurality of position sensors for generating a digitized bone data set comprising coordinates corresponding to the points; and performing a best-fit calculation between coordinates of the bone image data set and corresponding coordinates of the digitized bone data set to transform the bone image data set into the robotic coordinate system.

25. A method for transforming a bone image data set representing at least a partial image of a long bone to a robotic coordinate system, comprising:

provide a bone image data set comprising coordinates corresponding to a bone image;

operating a non-contact digitizing apparatus to generate a digitized bone data set representing points on the surface of the bone; and performing a best-fit calculation between coordinates of the bone image data set and corresponding coordinates of the digitized bone data set to transform the bone image data set into the robotic coordinate system.

26. A controller program for a robotic system having a surgical robotic arm operating in a robotic coordinate system and a bone digitizer arm, wherein the program transforms a bone image data set into the robotic coordinate system based upon surface location measurements generated by a plurality of position sensors in the bone digitizer arm, wherein the bone is immobilized in the robotic coordinate system.

* * * * *